United States Patent [19]

Timpl

[11] 4,340,581

[45] Jul. 20, 1982

[54] PROCESS FOR THE IMMUNOLOGICAL DETERMINATION OF BASAL MEMBRANE MATERIAL AND NEW BASAL MEMBRANE SUITABLE THEREFOR

[75] Inventor: Rupert Timpl, Krailing, Fed. Rep. of Germany

[73] Assignee: Max-Planck-Gesellschaft zur Forderung der Wissenschaften e.V., Gottingen, Fed. Rep. of Germany

[21] Appl. No.: 154,735

[22] Filed: May 30, 1980

[30] Foreign Application Priority Data

Jun. 11, 1979 [DE] Fed. Rep. of Germany ....... 2923583

[51] Int. Cl.[3] .................... G01N 33/56; G01N 33/58; C07G 7/00

[52] U.S. Cl. .................................... 424/1; 23/230 B; 424/12; 260/112 R

[58] Field of Search .................... 424/1, 12; 23/230 B; 260/112 R

[56] References Cited

PUBLICATIONS

Risteli et al., Anal. Biochem., 113, 372–378, 1981.

*Primary Examiner*—Christine M. Nucker

*Attorney, Agent, or Firm*—Felfe & Lynch

[57] ABSTRACT

This invention relates to a process for the immunological determination of basal membrane material in body fluids and provides new basal membrane fragments suitable for such determination, and a process for their preparation.

18 Claims, No Drawings

PROCESS FOR THE IMMUNOLOGICAL DETERMINATION OF BASAL MEMBRANE MATERIAL AND NEW BASAL MEMBRANE SUITABLE THEREFOR

This invention relates to a process for the immunological determination of basal membrane material in body fluids. In an additional aspect, the invention provides new basal membrane fragments suitable for such determination, and a process for their preparation.

It is well known that in a large number of diseases e.g. diabetes, nephropathologies, fibrosis of the liver, and vasculitis, an increase in the basal membranes appears, especially in the walls of the blood vessels. These changes in the blood vessel walls very frequently represent a lethal factor. Through immunofluorescent investigations of these diseases, it has now been found that a change in the basal membrane is based, among other things, on increased production of a new constituent of the basal membrane, which is designated as laminin, and of basal membrane collagen. Histological investigations, permit specific proof of these changes, but can only be carried out on biopsy material, and can not be evaluated quantitatively.

The present invention, therefore, is based on the objective of solving this problem by creating a quantitative and specific process for the determination of basal membrane antigens in the blood and other body fluids (the urine, the ascites). Another objective is to make definite basal membrane antigens available for this process.

This objective is achieved by means of a process for the immunological determination of basal membrane material in body fluids, characterized in that tagged laminin, tagged laminin fragment P1, or tagged basal membrane fragment 7S collagen is incubated as an antigen with its specific antibody in the presence of the sample to be tested, the antigen-antibody complex formed is separated, and the quantity of tagged antigen contained in the complex or in the separated fluid is determined.

The process according to the present invention is based on the characterization of three new structural proteins of the basal membrane, namely, of laminin, the laminin fragment laminin P1, and the collagen peptide 7S collagen. These three new substances, especially, however, the two fragments laminin P1 and 7S collagen, exhibit high stability with respect to proteolytic decomposition and denaturing influences, and therefore, appear in clearly identifiable quantities also in body fluids, especially in the blood, so that the increase in basal membranes can be established by means of their quantitative determination.

With laminin, it is a question of a high-molecular glycoprotein. It is characterized in that it is a glycoprotein with 12 to 15% by weight carbohydrate content and a molecular weight of 800 to 1000 k, consists of two kinds of disulfide-linked polypeptide chains with a molecular weight of about 220 k and 440 k, and can be obtained by means of the extraction of tissue containing basal membrane with concentrated salt solutions in the presence of protease inhibitors, subsequent extraction of the tissue with 0.4 to 0.6 M NaCl, precipitation of the latter extract with 3.3 to 3.5 M NaCl, and chromatography of the dissolved precipitate.

By degrading laminin with protease, such as pepsin, or according to chemical methods, for example, by means of cyanogen bromide, a large fragment can be obtained from this, which is designated as laminin P1. This fragment may also be obtained directly from tissue.

Laminin P1 is characterized in that it exhibits a molecular weight of 200 to 300 k, a cysteine content of 12 to 14% Mol, a great affinity for lectine and stability toward collagenase, and can be obtained by (1) the decomposition of laminin with a protease or cyanogen bromide or (2) by the extraction of tissue containing basal membrane with concentrated salt solutions, then with 0.4 to 0.6 M NaCl, in each case in the presence of protease inhibitors, incubation of the remaining residue with protease, dialysis of the solution obtained, fractional precipitation of the solution obtained between 2 M and 4 M NaCl, chromatography via a weakly basic cation-exchanger, and chromatography via lectin. Typical examples of lectins for which laminin P1 shows a great affinity are concanavalin A and wheat-germ lectin.

The third new antigen that can be used within the framework of the invention is a fragment of a disulfide-rich variant of basal-membrane collagen, and is resistant to both the usual proteases, such as, pepsin and trypsin, as well as to bacterial collagenase (Cl hystolyticum). It is designated as 7S collagen and is characterized in that it exhibits a molecular weight of 200 to 300 k, a cysteine content of 2 to 5% Mol, an axial ratio of the order of magnitude of 1:10, and a stable triple helix with a melting point in the range of 60° to 70° C., is resistant to collagenase, and can be obtained by the extraction of basal membrane-containing tissue with a concentrated salt solution and then with 0.4 to 0.6 M NaCl, in each case in the presence of protease inhibitors, incubation of the extraction residue with a protease, dialysis of the solution obtained, precipitation with 2 M NaCl, incubation of the redissolved precipitate with collagenase, dialysis, and chromatographic purification.

By comparison, the axial ratio for collagen is 1:200.

The table below indicates the amino acid composition of the three new antigens.

TABLE

| | 7s collagen | Laminin | Laminin P 1 |
|---|---|---|---|
| Hyp | 90 | — | — |
| Asp | 68 | 109 | 113 |
| Thr | 25 | 58 | 56 |
| Ser | 19 | 77 | 81 |
| Glu | 85 | 122 | 106 |
| Pro | 62 | 53 | 63 |
| Gly | 323 | 93 | 118 |
| Ala | 41 | 76 | 47 |
| Cys | 45 | 30 | 136 |
| Val | 28 | 48 | 40 |
| Met | 4 | 14 | 6 |
| Ile | 23 | 42 | 20 |
| Leu | 51 | 92 | 54 |
| Tyr | 13 | 27 | 28 |
| Phe | 12 | 31 | 30 |
| His | 15 | 24 | 33 |
| Hyl | 39 | 2 | 2 |
| Lys | 14 | 52 | 30 |
| Arg | 43 | 50 | 38 |

These new basal membrane constituents, which are designated below as antigens according to the present invention, make it possible, as has already been mentioned, to determine, according to the present invention, basal membrane material in body fluids, especially in the blood, with the use of immunological methods of detection that are in themselves well known, and that are based on the competition of a known quantity of tagged antigen with an unknown quantity of the antigen in the sample to be investigated for the common antibody. In so doing, the well-known radio-immunoassay (RIA) variants, as well as the enzyme-immunoassay variants and analogous determinations may also be employed with the use of other types of tagging, for example, fluorescent tagging, dye tagging, and the like. Such methods are well known to the expert, and shall not be presented in detail again here. All these processes are based on the fact that with the aid of antigens as highly purified as possible, an antiserum is prepared in suitable experimental animals; this is obtained as such or the specific antibodies isolated from it are obtained, and if necessary, after linking the antibodies or antisera to a solid carrier, the usual antigen-antibody-complex-formation reaction is carried out by incubating the reaction partners with each other. According to the quantity of untagged antigen present in the sample of body fluid to be investigated, only a part of the tagged antigen is bound in this complex, and can be measured either by isolation of the complex or in the supernatant liquid. Since the quantity of the tagged antigen that is bound in the complex is dependent on the quantity of the unbound antigen, the content of antigen-effective basal membrane material in the body fluid can be determined in this way.

The preparation of the antisera can take place in the usual way, by subcutaneous injection into experimental animals, preferably rabbits. In so doing, it is expedient to work in the presence of the complete Freund's adjuvant. The quantities of antigen customary in such cases can be administered. With the use of rabbits, 0.5 to 1 mg/animal proved to be an especially suitable dose. The antiserum formed is then obtained in the manner well known to the expert, and then used as such. It is also possible to purify beforehand the specific antibody present in the serum, for example, by affinity chromatography.

The tagging of the antigen can be carried out with the methods that are well known in the tagging of proteins. In the case of radioactive tagging with a radionuclide, iodine 125 is preferred for use as the latter. Tagging with this radionuclide can then be carried out according to the well known chloramine-T method (*Int. Arch. Allergy*, 29,185).

A preferred form of carrying out the process according to the present invention consists of separating the antigen-antibody-complex formed with the specific antiserum from the unbound antigen by the use of a second antibody. In so doing, the use of an antibody against immunoglobulin G of the species of animal used to obtain the antiserum is preferred as the second antibody. The separation of the antigen-antibody-complex that is converted with it into insoluble form from the solution can be carried out according to usual methods, such as, centrifuging off, filtering off, and the like. Alternatively, the antiserum or antibody is bound to a solid carrier, for example, the inner wall of a test tube.

After separating the antigen-antibody-complex, the tagging, for example therefore, the radioactivity or the enzyme activity that is bound in the antigen-antibody-complex, or, as one chooses, has also remained in the supernatant liquid, is determined as mentioned. The quantity of antigen contained in the sample to be investigated can then be determined on the basis of a calibration curve that has been prepared by means of samples of known antigen content. In principle, the more untagged antigen present in the sample to be determined, the smaller the quantity of the tagged antigen which is bound in the antigen-antibody complex that has been formed.

The immunological determination process according to the present invention permits the measurement of concentrations up to the range of 1 ng/ml. It is, thus, possible to use this process for the determination of basal membrane material in animal and human body fluids, especially in the blood or serum. In normal individuals, the concentration of these antigens in the serum lies in the range of 20 to 50 ng/ml, and increases with basal membrane changes to a significant extent, as has been observed, for example, in experimental diabetes. With the aid of the process according to the present invention, such changes can now be found relatively quickly and surely.

The new antigens used in the process according to the preent invention can, in principle, be obtained from all tissues that contain basal membranes. Human placenta is preferred, since the content of material to be obtained is clearly greater there. Also preferred are special tumor tissues, which produce large quantities of basal membrane, such as, for example, EHS-sarcoma of mice.

In obtaining the new antigens in accordance with the present invention, any preparation of basal membrane in the pure state from these tissues has been foregone. The tissues are first extracted with high salt concentrations in the presence of protease inhibitors, and in so doing accompanying proteins are removed. For this, 3.4 to 4 M NaCl is preferred. The tissue is, naturally, first comminuted or homogenized in the usual way for the extraction. After repeated extraction, if necessary, with a high salt concentration, a second extraction step is carried out with a low salt concentration, expediently with 0.4 to 0.6 M NaCl, and this can also be carried out several times. In so doing, practically no basal membrane collagen goes into solution, but a part of the laminin is dissolved out. The solution obtained in this way can be used to obtain the laminin P1 of the laminin and the laminin fragment, while the insoluble tissue residue that has remained in the double salt extraction serves as the starting material for obtaining the fragment 7S collagen, but is also suitable for the production of laminin P1.

As protease inhibitors, for example, phenyl methylsulfonyl fluoride, p-chloromercuric benzoate, or ethylene diamine tetra cetic acid are used as protease inhibitors. Other protease inhibitors are also suitable, however. The inhibitors may be used individually or mixed. Suitable concentrations are usually between about 1 to 50 mg/l.

Native laminin can be separated from the extract containing laminin by means of salt precipitation of accompanying proteins. Preferably, the precipitation is accomplished with 3.3 to 3.5 M NaCl.

The precipitate obtained in this way is taken up in a buffer again and subjected to chromatography, for example, with agarose A1.5m. In this manner, the laminin described above is obtained, which can be used in the manner described for the process according to the present invention.

The fragment P1 can be prepared from the laminin obtained in this way by decomposition with a proteolytic enzyme or using chemical means, such as with cyanogen bromide. Preferably, the decomposition takes place with pepsin in a strongly acid solution with a pH of about 1.5 to 2.5. The fragment P1 can be prepared by fractional salt precipitation from the solution obtained in this way. Preferably, the precipitation takes place first with 2 M NaCl, and then with 4 M NaCl, and in so doing, the laminin P1 precipitates with the last step.

Alternatively, the fragment P1 can be prepared directly from basal membrane material, which does not have to be isolated. In this preferred method of preparation, one proceeds from the insoluble tissue residue of the two-stage salt extraction. The residue is put into suspension, and incubated with a proteolytic enzyme under the conditions of temperature and pH-value that are suitable for this enzyme. Preferably, pepsin is used, and the work is carried out at a pH value of about 1.5 to 2.5 at normal temperature or insignificantly lower temperatures. Temperatures of about 10° to 20° C. are well suited. After that, it is separated from the insoluble material, the lower molecular material is removed by dialysis, and the laminin P1 is obtained from the resulting solution by salt fractionation in the manner described above. The precipitation preferably takes place first with 2 M NaCl, and then with 4 M NaCl.

The laminin P1 can be further purified by chromatography from the precipitated fraction of 2 to 4 M NaCl. It is preferable to carry out the chromatography first on a weakly basic cation-exchanger, such as DEAE-cellulose or DEAE-Sephadex. A fine-purification can then take place by binding to lectin that is present in insoluble form, for example, by binding to a carrier or by cross-linking, and subsequent elution with a suitable carbohydrate. A gel filtration, for example, with cross-linked dextran, such as agarose A1.5M, may also be used for purification.

To obtain the fragment 7S collagen, one also proceeds from the decomposition solution of the tissue, which has been extracted with salt solutions in two stages. The precipitate obtained after protease treatment up to 2 M NaCl, after dissolving again with collagenase, is incubated under conditions of temperature and pH-value that are suitable for this enzyme, and by so doing, all the other collagens, except 7S collagen, are decomposed, and can be removed by dialysis. The fine-purification can then be carried out by means of molecular-screen chromatography, for example, with cross-linked dextran or/and carboxymethyl cellulose.

Pepsin is, as a matter of fact, preferred for the proteolytic processing steps described above, but other proteases, such as trypsin, are also suitable here. Alternatively, a chemical decomposition process may also be used. This is preferably carried out with cyanogen bromide.

The following examples explain the present invention in detail.

EXAMPLE 1

Preparation of the Tagged Antigen

25 μg of laminin P1 or peptide 7S collagen are tagged with 0.5 millicurie iodine 125 according to the chloramine-T method, and unbound iodine is removed by dialysis or gel filtration with Biogel P-2. The further steps are preferably carried out in the presence of 0.04% of a non-ionic detergent, such as, for example, Tween 20. Binding curves with the antibody are determined with 1 ng of tagged peptide.

Carrying Out the Immunological Determination (RIA)

The concentration of laminin P1 or 7S collagen in an unknown sample of serum or of other body fluids is determined in the following inhibition test. A certain quantity of the specific antibody or antiserum is preincubated with the unknown sample for 16 hours at 4° C., and after adding 1 ng of tagged antigen, it is incubated for 8 hours more at 4° C. Then an excess of the antibody for rabbit immunoglobulin G is added, and after 16 hours more at 4° C., the antigen bound in the immunocomplex is removed by centrifuging. The inhibiting activity of the unknown sample is compared with the activity of a standard concentration of untagged antigen.

EXAMPLE 2

The Preparation of Laminin

Human placenta or a transplantable mouse tumor (EHS-sarcoma, described in Orkin et al., *J. Exp. Med.*, 145 (1977): 204–220) is used as the starting material. The tissue is first homogenized two or three times in a 20-fold excess of 3.4 M NaCl, 0.05 Tris. HCl, pH 7.4, in the presence of the protease inhibitors phenyl methyl sulfonyl fluoride (3 mg/l), p-chloromercuric benzoate (3 mg/l) and ADTA (0.01 M), and extractable protein is removed by centrifuging. The residue is then extracted twice with 0.5 M NaCl, 0.05 Tris. HCl, pH 7.4, in the presence of protease inhibitors at 4° C. overnight. The extract contains native laminin, which is separated from accompanying protein by precipitation with 3.4 M NaCl and chromatography of the precipitate, which is dissolved again, with agarose A1.5m (1 M$CaCl_2$), 0.05 M Tris. HCl, pH 7.4.

EXAMPLE 3

Preparation of the Peptide Laminin P1

The insoluble tissue residue that remains after the salt extractions described in Example 2 is homogenized in 0.5 M acetic acid (50 mg/g dry weight), the pH-value is adjusted to 2 by adding HCl, and the suspension, after adding pepsin (50 mg/g dry weight) is incubated for 24 hours at 15° C. The enzymatically dissolved material is isolated by centrifuging, and dialyzed at 4° C. against 0.5 M NaCl, 0.05 M Tris, pH 7.4. A mixture of collagenous proteins is precipitated from this solution with 2 M NaCl, and the fragment laminin P1 is concentrated by the subsequent precipitation of the supernatant liquid with 4 M NaCl. The precipitate up to 2 M NaCl can be used for the preparation of 7S collagen.

Laminin P1 is further purified from the precipitate (2 to 4 M NaCl) with DEAE-cellulose, which is equilibrated in 0.05 M Tris.HCl, pH 8.6, 2 M urea, and is eluted with a linear NaCl-gradient (0 to 0.4 M). The final purification is carried out by binding to a Concanavalin A-column and elution with 0.1 M α-methyl mannoside. If necessary, a further purification may be carried out by gel filtration with agarose A1.5m. Alternatively, laminin, which is obtained according to Example 2, may be used in place of the tissue residue.

EXAMPLE 4

The Preparation of 7S collagen

To isolate peptide 7S collagen, the mixture of collagenous proteins (precipitate 0.5 to 2 M NaCl) that is obtained according to Example 3 is dissolved in 0.05 M Tris.HCl, pH 7.4, 0.2 M NaCl, 0.002 M $CaCl_2$ (10 mg/ml), and after the addition of bacterial collagenase (0.1 mg/ml), it is incubated for 16 hours at 20° or 37° C. In so doing, all the other collagens, with the exception of the peptide Col 1(IV), are decomposed to lower molecular peptides, which are removed by dialysis. Further purification takes place with agarose A5M (1M CaCl, 0.05 M Tris.HCl, ph 7.4) and subsequent binding of the peptide to a column of CM-cellulose, which was equilibrated in 0.01 M sodium acetate, pH 4.0, 4 M urea. Pure 7S collagen is eluted from the column by means of a linear NaCl-gradient (0 to 0.2 M NaCl).

It will be understood that the specification and examples are illustrative, but not limitative of the present invention and that other embodiments within the spirit and scope of the invention will suggest themselves to those skilled in the art.

What is claimed is:

1. Process for the immunological determination of basal membrane material in body fluids, which process comprises incubating a tagged basal membrane antigen selected from tagged laminin, tagged laminin fragment P1 and tagged basal membrane fragment 7S collagen, with a first antibody specific to said antigen in the presence of the body fluid sample to be tested, whereby antigens in the body fluid sample will compete with said tagged antigen for said antibody, separating the antigen-antibody-complex formed, and determining the quantity of tagged antigen contained in the complex or in the separated liquid as a measure of the basal membrane material contained in said body fluid.

2. Process as claimed in claim 1 wherein the antigen is tagged radioactively.

3. Process as claimed in claim 1 wherein the antigen is tagged enzymatically.

4. Process as claimed in claim 1 wherein the antigen is fluorescence tagged.

5. Process as claimed in claim 1 wherein the first antibody is from an antiserum raised in a suitable animal species and the step of separating the antigen-antibody complex includes adding, a second antibody which second antibody is against the immunoglobulin G of the animal species used for the preparation of the antiserum.

6. Process as claimed in claim 1 wherein the antibody or anti-serum is bound to a solid carrier.

7. Process as claimed in claim 1 wherein said first antibody is in the form of rabbit anti-serum or antibody.

8. Laminin suitable for the immunological determination of basal membrane material in body fluids, comprising a glyco protein of 12 to 15% by weight carbohydrate content and a molecular weight of 800 to 1,000 k, consisting of two disulfide-linked polypeptide chains of a molecular weight of about 220 to 440 k.

9. Laminin fragment P1 suitable for the immunological determination of basal membrane material in body fluids, having a molecular weight of 200 to 300 k, a cysteine content of 12 to 14% Mol, and a high degree of affinity for lectin and stability toward collagenase.

10. Basal membrane peptide 7S collagen suitable for the immunological determination of basal membrane material in body fluids, having a molecular weight of 200 to 300 k, a cysteine content of 2 to 5% Mol, and axial ratio of the order of 1:20, a stable triple helix with a melting point in the range of 60° to 70° C., and resistent to collagenase.

11. Process for the preparation of the of claim 8 comprising extracting a tissue material containing a basal membrane in the presence of protease inhibitors, first with high salt concentrations, then with 0.4 to 0.6 M NaCl, separating the laminin by salt precipitation from the extract using 0.4 to 0.6 M NaCl, and optionally dissolving the precipitate and subjecting same to chromatography.

12. Process for the preparation of laminin fragment P1 comprising extracting tissue containing basal membrane with a concentrate of salt solution of 0.4 to 0.6 M NaCl, dialyzing the solution obtained containing the fraction precipitated between 2 M and 4 M NaCl from the dialyzed solution, and subjecting same to the chromatography with a weakly basic cation-exchanger and with lectin.

13. Process for the preparation of laminin as claimed in claim 8 comprising incubating laminin with protease, dialyzing the solution obtained containing the fraction precipitated between 2 M and 4 M NaCl from the dialyzed solution, and subjecting same to chromatography with a weakly basic cation-exchanger and with lectin.

14. Process for the preparation of basal membrane peptide 7S collagen suitable for the immunological determination of basal membrane material, which process comprises extracting tissue containing basal membrane in the presence of protease inhibitors with concentrated salt solutions and then with 0.4 to 0.6 M NaCl, incubating same with a protease, dialyzing the resulting solution, precipitating the 7S collagen from the dialyzed solution with 2 M NaCl, dissolving the precipitate, incubating same with collagenase, and the dialyzing and subjecting the incubate to chromatography.

15. Process as claimed in claim 11 wherein the tissue material containing a basal membrane is human placenta or mouse EHS-sarcoma.

16. Process as claimed in claim 12 wherein the tissue material containing a basal membrane is human placenta or mouse EHS-sarcoma.

17. Process as claimed in claim 13 wherein the tissue material containing a basal membrane is human placenta or mouse EHS-sarcoma.

18. Process as claimed in claim 14 wherein the tissue material containing a basal membrane is human placenta or mouse EHS-sarcoma.

* * * * *

UNITED STATES PATENT AND TRADEMARK OFFICE
CERTIFICATE OF CORRECTION

PATENT NO. : 4,340, 581
DATED : July 20, 1982
INVENTOR(S) : Rupert Timpl

It is certified that error appears in the above-identified patent and that said Letters Patent are hereby corrected as shown below:

| Column | Line | Correction |
| --- | --- | --- |
| 6 | 68 | Delete "Col-1(IV)" and insert -- 7S Collagen --. |
| 8 (Claim 11 | 10 1) | After "preparation of the" insert -- laminin --. |

Signed and Sealed this

*Twenty-sixth* Day of *April 1983*

[SEAL]

*Attest:*

GERALD J. MOSSINGHOFF

*Attesting Officer* *Commissioner of Patents and Trademarks*